United States Patent [19]
Wool

[11] Patent Number: 5,624,258
[45] Date of Patent: Apr. 29, 1997

[54] ORTHODONTIC ARCH WIRE AND APPLIANCE EMPLOYING THE SAME

[76] Inventor: Arthur L. Wool, 267 Faust Rd., Sinking Spring, Pa. 19608

[21] Appl. No.: 372,162

[22] Filed: Jan. 12, 1995

[51] Int. Cl.⁶ .................................................. A61C 3/00
[52] U.S. Cl. ............................................................ 433/20
[58] Field of Search ............................................... 433/20

[56] References Cited

U.S. PATENT DOCUMENTS

| | | | |
|---|---|---|---|
| 4,571,179 | 2/1986 | Balenseifen | 433/20 |
| 4,818,226 | 4/1989 | Berendt et al. | 433/20 |
| 5,167,499 | 12/1992 | Arndt et al. | 433/20 X |
| 5,288,230 | 2/1994 | Nikutowski et al. | 433/20 |
| 5,344,315 | 9/1994 | Hanson | 433/20 |

*Primary Examiner*—Robert P. Swiatek
*Assistant Examiner*—Elizabeth Shaw
*Attorney, Agent, or Firm*—Antonelli, Terry, Stout & Kraus, LLP

[57] ABSTRACT

An orthodontic arch wire, comprising a continuous wire having a generally parabolic shape defining a principal plane, the wire having a bend extending substantially in the principal plane, the bend being located approximately midway along a length of the wire, and an orthodontic appliance employing the wire.

14 Claims, 2 Drawing Sheets

ORTHODONTIC ARCH WIRE AND APPLIANCE EMPLOYING THE SAME

BACKGROUND OF THE INVENTION

This invention relates to orthodontics and, in particular, to a new and improved orthodontic arch wire, and orthodontic appliance employing the arch wire.

In the field of orthodontics, it is conventional to use an arch wire to correct irregularities and/or abnormalities in the relationship between various teeth. It is conventional to apply wire-receiving brackets to the teeth with the exception of the distal molars to which tubes are applied. A parabolic arch wire is inserted to the wire-receiving slots of the brackets on the teeth and the ends of the arch wire are inserted and received by the molar tubes. Ligature wires or o-rings are used to prevent the arch wire from slipping out of the slots in the brackets. When attached to the brackets, the wires under flexural and/or torsional stresses which, due to the resiliency of the wire, exert corrective tooth-moving forces on the teeth.

As explained in U.S. Pat. No. 4,900,251 to Andreasen, the contents of which are incorporated herein by reference, it was customary, when using stainless steel arch wires, to form bends in the distal ends thereof immediately at the distal ends of the molar tubes to prevent mesial-distal movement. However, as is well known in the art, it is now not uncommon to form arch wires of shape memory alloys, the physical properties of which resist the formation of an effective distal bend. While arch wires formed of shape memory alloys have a number of advantages, they suffer from the disadvantage that they are typically free to slide in a mesial-distal direction until one end protrudes excessively from a molar tube so it contacts and irritates the patient's mouth. This is due to the fact that the arch wires made of shape memory alloys have a relatively low coefficient of friction and cannot be effectively bent at their distal end.

The aforementioned U.S. Pat. No. 4,900,251 to Andreasen, as well as U.S. Pat. No. 4,892,479 to McKenna, the contents of which are incorporated herein by reference, each disclose an orthodontic arch wire provided at its mid-point or vertex with a bend or dimple shown to be substantially perpendicular to the principal plane of the arch wire. The bend impedes movement of the arch wire since the bend can not slip past the wire-receiving slots of the brackets mounted on the patient's central incisors because the dimple is measurably larger than the vertical clearance afforded by the bracket slots.

While the "vertical" bend disclosed in the McKenna and Andreasen patents can be effective in impeding mesial-distal slippage of the arch wire, arch wires having such a vertical bend suffer from a number of disadvantages. One such disadvantage is that such arch wires are aesthetically unsatisfactory since a bend outside the principal plane of the arch wire is very noticeable when the arch wire is installed in the patient's mouth.

Arch wires having a vertical bend are also disadvantageous in connection with treatment of a rotated central incisor. Specifically, in order to engage a rotated central incisor, a leg of the vertical bend must be distorted out of its original plane often leading to rotation of the bend out of its original vertical plane. The urge to correct the tooth rotation by the elastic return to the arch wire's original formation is compromised by the fact that the arch wire with the vertical bend is not able to exert the same degree of rotational effort in this situation. This is especially true in the cases of rotated lower central incisors (as can be attested by orthodontic clinicians who refuse to use such vertically dimpled arches in such cases).

As will be understood by those skilled in the art, arch wires of the type depicted in the Andreasen and McKenna patents, i.e., having a vertical bend, will also be disadvantageous in connection with arch shifting. Arch shifting may be necessary to correct a poor bite that is in malocclusion and requires the movement of all the patient's upper teeth to the patient's left and/or all of the lower teeth to the patient's right or vice versa. In this case, elastics supply the moving force and extend between hooks and distal tubes fastened to the upper and lower arches. As is known in the art, during arch shifting, the hooks frequently become wedged against a bracket. For this reason, the hooks are able to be loosened by the orthodontist and shifted as necessary. However, using an arch wire having a vertical bend, as disclosed in the Andreasen and McKenna patents, would also involve the disadvantage that the vertical bend, during arch shifting, will become wedged against one of the central incisor brackets, preventing further shifting and further correction.

Arch wires having a vertical bend are also more difficult to manufacture, thus increasing their costs.

SUMMARY OF THE INVENTION

The present invention provides an orthodontic arch wire which impedes mesial-distal slippage but overcomes the disadvantages of arch wires having a vertical bend.

The orthodontic arch wire of the present invention is a continuous wire having a generally parabolic shape defining a principal plane of the arch wire. The wire has a bend extending substantially in that principal plane, the bend being located approximately midway along a length of the wire. The orthodontic arch wire of the present invention can be used in an orthodontic appliance which includes at least two brackets mounted on adjacent central incisors of a patient, the two brackets having wire receiving slots therein, and the orthodontic arch wire being provided in the wire-receiving slots. The orthodontic arch wire is retained in the wire-receiving slots by use of retaining means, such as o-rings or ligature wires. The arch wires of this invention may be composed of stainless steel, nickel-chrome-cobalt, nickel titanium, or any of the various alloys used in orthodontics and may be of unitary cross-section, braided, or twisted.

DETAILED DESCRIPTION OF THE PREFERRED EMBODIMENTS

Figure 1:
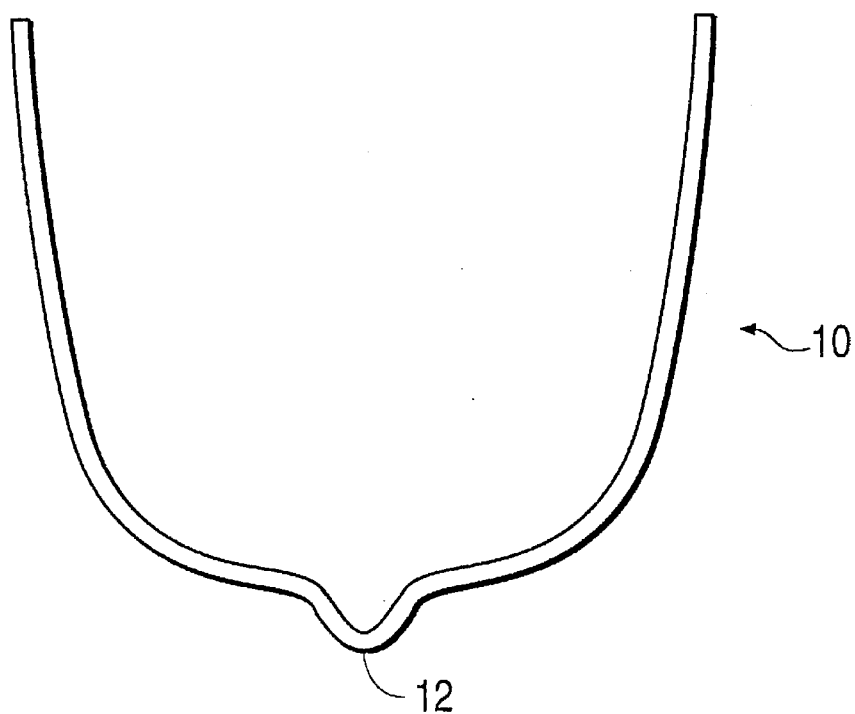
FIG. 1 is a top plan view of an arch wire according to the present invention.

FIG. 1 shows the arch wire 10 of the present invention. The arch wire is formed into a generally U-shape or parabolic shape. The vertex of the parabola or mid-point area of the arch will be located at the center of the dental arch of the patient where it will lie between orthodontic brackets which are mounted on the central incisors, as will be explained hereinafter in connection with FIG. 3. The wire of the present invention is conventional with the exception of its mid-point or vertex. Thus, the wire may have a rectangular, square, or round cross section and can be formed from materials known and used in the art. However, the novel features of the present invention are particularly advantageous when used in connection with arch wires formed of an ultra-elastic or shape memory alloy such as nitinol, a well known alloy of nickel and titanium. The wire may have a cross-sectional size in the range of 0.012" to 0.020" round and various rectangular or square cross-sections from 0.016"×0.016" to 0.022"×0.028". The arch wire shown in FIG. 1 has a bend 12 formed at the vertex or mid-point of the wire. The bend 12 extends away from the otherwise parabolic shape of the wire in a direction which, when the wire is installed in the patient's mouth will be toward the anterior of the patient's mouth, i.e., in the labial direction.

Figure 2:
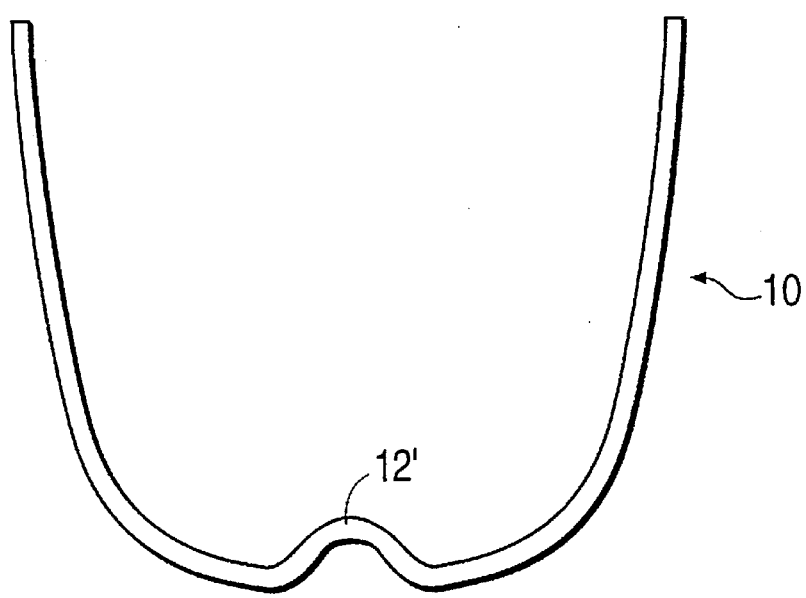
FIG. 2 is a top plan view of another embodiment of an arch wire of the present invention.

FIG. 2 shows another embodiment of an arch wire of the present invention wherein the bend 12' provided at the vertex or mid-point of the arch wire 10 extends away from the otherwise parabolic shape of the arch wire 10 in a direction designed to be to the posterior of the patient's mouth, i.e., in the palatal direction.

In the embodiments shown in both FIGS. 1 and 2, the bend 12 or 12' extends substantially in the plane of the arch wire which, in connection with FIGS. 1 and 2, is within the plane of the paper.

Figure 3:
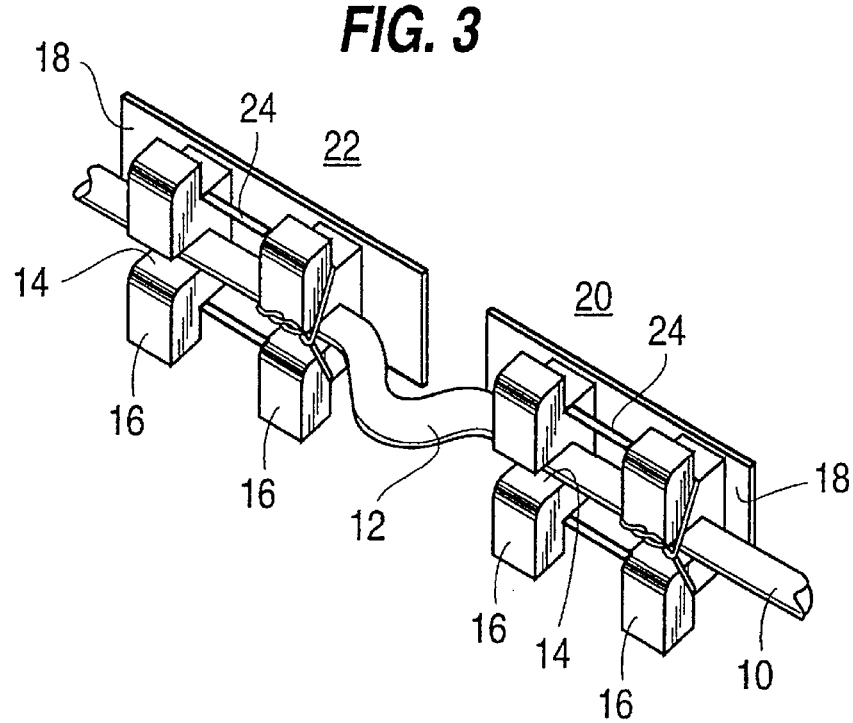
FIG. 3 is a perspective view of an orthodontic appliance, including the arch wire of FIG. 1 which is mounted on brackets attached to the central incisors of an orthodontic patient.

FIG. 3 shows the arch wire 10 of the present invention mounted in wire-receiving slots 14 of wings 16 of conventional siamese brackets 18. The siamese brackets 18 are shown attached to central incisor teeth 20 and 22 of a patient's mouth. The brackets 18 can be attached to the teeth by any means known in the art, such as with adhesive or with a circumferential band. Of course, as those skilled in the art will understand, brackets other than the siamese brackets shown in FIG. 3 may be used.

The arch wire 10 is held in the brackets 18 by retaining means which, in the embodiment shown in FIG. 3, comprise ligature wires 24. As will be understood by those skilled in the art, any conventional retaining means, including o-rings, can be used.

Figure 4:
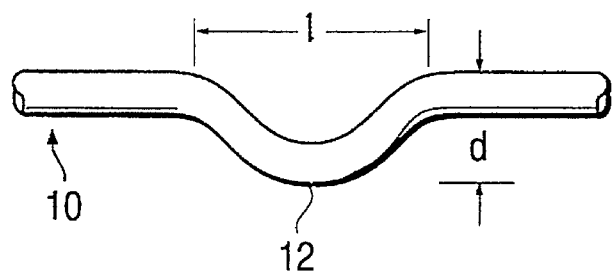
FIG. 4 is a top plan view of the bent portion of an arch wire according to the present invention.

As can be appreciated, the bend 12 of the arch wire 10 is such that sliding of the arch wire 10 in a mesial-distal direction is impeded when the bend 12 contacts the retaining means (e.g., ligature, wire 24 or o-ring) used to retain the arch wire 10 in the slots 14 of the brackets 18. The size and shape of the bend can be selected to ensure this effect and, in part, depends on the dimension of the wire-receiving slots 14 and diameter of the arch wire 10 and the interproximal distance between adjacent sides of the brackets on the central incisors. For example, the bend may have, as shown in FIG. 4, a length l in a range of 1–6 mm and as offset d in the range of 1–4 mm; more specifically the bend may have a length l of 1–3 mm in a lower arch and an offset d in the range of 1–2 mm, and a length l in the range of 3–5 mm in an upper arch and an offset d in the range of 1–2 mm. As will be understood by those skilled in the art, the length is measured in the mesial-distal direction while the offset is measured in the labial-palatal direction.

Figure 5:
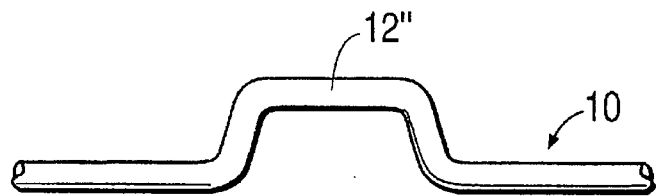
FIG. 5 is a top plan view of the bent portion of another embodiment of an arch wire according to the present invention.

While FIGS. 1 to 4 show a generally V-shaped bend 12 or 12', the bend may have other shapes, such as the U-shape shown in FIG. 5.

Since the bend 12, 12' or 12" extends substantially in the same plane as the arch wire 10, the bend is not noticeable from a face-to-face view of the patient's mouth. That is, the side elevational view of the arch wire 10 of the present invention appears substantially similar to parabolic shaped arch wires without a bend at their mid-points or vertices. Thus, the arch wire 10 of the present invention is more advantageous aesthetically than arch wires with vertical bends such as those described in the aforementioned patents to Andreasen and McKenna.

As can also be appreciated by those skilled in the art, the arch wire of the present invention, e.g., the arch wire shown in FIG. 1, can be used to treat a rotated central incisor tooth without any of the disadvantages described in connection with arch wires having a vertical bend. Moreover, since the bend is provided in the same plane as the arch wire, the bend will not become wedged in a bracket during correction of a malocclusion which requires movement of all of the patient's upper or lower teeth in one direction. This is because, according to the present invention, it is retaining means, such as ligature wire 24, which impedes the mesial-distal movement of the arch wire 10, not the brackets themselves.

The arch wire 10 of the present invention can be manufactured by means which will be appreciated by those skilled in the art. For example, the wire may be bent into a parabolic shape, e.g., by wrapping the wire around a mandrel, subsequently bending the wire 10 to have a bend 12, 12' or 12" and heat-setting the bent wire 10. The bend in the arch wire may be formed, e.g., by placing the arch wire between two mating forming dies, the dies having the form of the desired bend machined into them to create a mating pair. One die may be stationary while the other die travels towards it. When the dies meet, the arch wire is formed to the desired shape. Heat may be introduced at this point in order to set the proper shape into the arch wire. After several seconds, the moveable die can be retracted to allow the operator to remove the arch wire. As an alternative manufacturing method, it may be advantageous for the mandrel around which the wire is bent to itself have a provision for forming the bend 12, 12' or 12".

As will be apparent to those skilled in the art, various modifications of the disclosed embodiments can be made without departing from the teachings of the present invention.

What is claimed is:

1. An orthodontic arch wire, comprising a continuous wire having a generally parabolic shape defining a principal plane, said wire having a bend extending substantially in said principal plane, said bend being located approximately midway along a length of said wire and having a length in a mesial-distal direction of 1–6 mm and an offset in a labial or palatal direction of 1–4 mm.

2. An orthodontic arch wire according to claim 1, wherein said wire is made of a shape memory alloy.

3. An orthodontic arch wire according to claim 1, wherein said wire is made of a nickel-titanium alloy.

4. An orthodontic arch wire according to claim 1, wherein said wire is made of a nickel-chrome-cobalt alloy.

5. An orthodontic arch wire according to claim 1, wherein said wire is made of a stainless steel.

6. An orthodontic arch wire according to claim 1, wherein said offset is in a labial direction.

7. An orthodontic arch wire according to claim 1, wherein said offset is in a palatal direction.

8. An orthodontic appliance comprising:
two brackets mountable on adjacent central incisors of a patient, each of said brackets having wire receiving slots;
an orthodontic arch wire provided in said wire-receiving slots, said orthodontic arch wire comprising a continuous wire having a generally parabolic shape defining a principal plane, said wire having a bend extending substantially in said principal plane, said bend being located approximately midway along a length of said wire; and retaining means for retaining said orthodontic wire in said wire receiving slots, wherein said bend impedes mesial-distal movement of said orthodontic arch wire.

9. An orthodontic appliance according to claim 8, wherein said wire is made of a shape memory alloy.

10. An orthodontic appliance according to claim 8, wherein said wire is made of a nickel-titanium alloy.

11. An orthodontic appliance according to claim 8, wherein said wire is made of a nickel-chrome-cobalt alloy.

12. An orthodontic appliance according to claim 8, wherein said wire is made of a stainless steel.

13. An orthodontic appliance according to claim 8, wherein said bend has a length in a mesial-distal direction of 1–6 mm and an offset in a labial direction of 1–4 mm.

14. An orthodontic appliance according to claim 8, wherein said bend has a length in a mesial-distal direction of 1–6 mm and an offset in a palatal direction of 1–4 mm.

* * * * *